(12) United States Patent
Reynolds et al.

(10) Patent No.: US 9,895,266 B2
(45) Date of Patent: Feb. 20, 2018

(54) GOGGLE LENS CHANGING SYSTEM

(71) Applicant: Spy Optic Inc., Carlsbad, CA (US)

(72) Inventors: Brittany Kay Reynolds, Carlsbad, CA (US); Keith Larronde Asher, Encinitas, CA (US)

(73) Assignee: Spy Optic Inc., Carlsbad, CA (US)

( * ) Notice: Subject to any disclaimer, the term of this patent is extended or adjusted under 35 U.S.C. 154(b) by 168 days.

(21) Appl. No.: 14/882,789

(22) Filed: Oct. 14, 2015

(65) Prior Publication Data

US 2017/0105874 A1 Apr. 20, 2017

(51) Int. Cl.
*A61F 9/02* (2006.01)

(52) U.S. Cl.
CPC ..................... *A61F 9/025* (2013.01)

(58) Field of Classification Search
CPC ................. A61F 9/025; A61F 9/026
See application file for complete search history.

(56) References Cited

U.S. PATENT DOCUMENTS

| | | | |
|---|---|---|---|
| 2,526,737 A | 10/1950 | Farina | |
| 3,056,140 A | 10/1962 | Lindbolm | |
| 3,298,031 A | 1/1967 | Morgan | |
| 3,363,262 A | 1/1968 | Lindbolm | |
| 3,377,626 A | 4/1968 | Smith | |
| 3,395,406 A | 8/1968 | Smith | |
| 3,505,680 A | 4/1970 | Ring | |
| 3,533,686 A | 10/1970 | O'Shea | |
| 3,754,298 A | 8/1973 | Menil | |
| 3,783,452 A | 1/1974 | Benson et al. | |
| 3,825,953 A | 7/1974 | Hunter | |
| 3,896,496 A | 7/1975 | Leblanc et al. | |
| 3,924,271 A | 12/1975 | Hirschmann, Jr. | |
| 3,931,646 A | 1/1976 | Loughner | |
| 3,945,044 A | 3/1976 | McGee et al. | |
| 4,011,595 A | 3/1977 | Shields | |
| 4,149,276 A | 4/1979 | Castro | |
| 4,150,443 A | 4/1979 | McNeilly | |
| 4,176,410 A | 12/1979 | Matthias | |
| 4,264,987 A | 5/1981 | Runckel | |
| 4,290,673 A | 9/1981 | Yamamoto | |
| 4,317,240 A | 3/1982 | Angerman et al. | |
| 4,425,669 A | 1/1984 | Grendol et al. | |

(Continued)

FOREIGN PATENT DOCUMENTS

| | | |
|---|---|---|
| CA | 2456476 | 3/2004 |
| DE | 2063092 | 7/1971 |

(Continued)

*Primary Examiner* — Shaun R Hurley
*Assistant Examiner* — Andrew W Sutton
(74) *Attorney, Agent, or Firm* — Stetina Brunda Garred & Brucker

(57) ABSTRACT

A goggle having a lens changing system is disclosed that includes a sliding lever that is traversable between a closed and opened position. The sliding lever, in the opened position, allows the lens to be released from the frame so that the user can either switch out the lens to a different lens that would be more appropriate for the current lighting conditions or to replace the current lens which may be defective. Additionally, the lens changing system has a nub and hole combination that further secures the lens to the frame so that the lens does not inadvertently dislodge off of the frame during active sports.

7 Claims, 7 Drawing Sheets

(56) References Cited

U.S. PATENT DOCUMENTS

| | | | |
|---|---|---|---|
| 4,428,081 | A | 1/1984 | Smith |
| 4,443,893 | A | 4/1984 | Yamamoto |
| 4,447,914 | A | 5/1984 | Jannard |
| 4,455,689 | A | 6/1984 | Boyer |
| 4,528,701 | A | 7/1985 | Smith |
| 4,556,995 | A | 12/1985 | Yamamoto |
| 4,571,748 | A | 2/1986 | Carroll et al. |
| 4,603,442 | A | 8/1986 | Barfield |
| 4,698,838 | A | 9/1987 | Angermann |
| 4,707,863 | A | 11/1987 | McNeal |
| 4,716,601 | A | 1/1988 | McNeal |
| 4,868,929 | A | 9/1989 | Curcio |
| 4,918,753 | A | 4/1990 | Mermillod |
| 4,977,627 | A | 12/1990 | Metcalfe et al. |
| 4,989,274 | A | 2/1991 | Patelski et al. |
| 5,018,223 | A | 5/1991 | Dawson et al. |
| 5,027,443 | A | 7/1991 | Watkins |
| 5,046,200 | A | 9/1991 | Feder |
| 5,056,163 | A | 10/1991 | Chou |
| 5,069,541 | A | 12/1991 | Holmes et al. |
| 5,093,940 | A | 3/1992 | Nishiyama |
| 5,138,723 | A | 8/1992 | Bolle |
| 5,182,817 | A | 2/1993 | Branum |
| D334,758 | S | 4/1993 | Reymondet et al. |
| 5,213,241 | A | 5/1993 | Dewar et al. |
| 5,216,759 | A | 6/1993 | Hewitt et al. |
| 5,339,119 | A | 8/1994 | Gardner |
| 5,341,516 | A | 8/1994 | Keim |
| D351,850 | S | 10/1994 | Bolle |
| 5,363,512 | A | 11/1994 | Grabos, Jr. et al. |
| 5,371,555 | A | 12/1994 | Nagel |
| 5,406,340 | A | 4/1995 | Hoff |
| D358,159 | S | 5/1995 | Lai |
| 5,410,763 | A | 5/1995 | Bolle |
| 5,421,037 | A | 6/1995 | Schulze |
| 5,423,092 | A | 6/1995 | Kawai |
| 5,452,480 | A | 9/1995 | Ryden |
| 5,471,036 | A | 11/1995 | Sperbeck |
| D367,664 | S | 3/1996 | Simioni |
| 5,495,623 | A | 3/1996 | Leonardi |
| 5,517,700 | A | 5/1996 | Hoffman |
| D371,566 | S | 7/1996 | Kolada et al. |
| 5,542,130 | A | 8/1996 | Grabos et al. |
| 5,617,588 | A | 4/1997 | Canavan et al. |
| 5,628,072 | A | 5/1997 | Haslbeck |
| 5,636,388 | A | 6/1997 | Hodges |
| 5,642,530 | A | 7/1997 | Parks |
| 5,650,866 | A | 7/1997 | Haslbeck |
| 5,652,965 | A | 8/1997 | Crooks |
| 5,655,228 | A | 8/1997 | Chiang |
| 5,657,106 | A | 8/1997 | Herald, Jr. et al. |
| 5,657,493 | A | 8/1997 | Ferrero et al. |
| 5,685,022 | A | 11/1997 | Essman et al. |
| 5,687,428 | A | 11/1997 | Yamamoto |
| 5,689,834 | A | 11/1997 | Wildon |
| 5,711,035 | A | 1/1998 | Haslbeck |
| D390,248 | S | 2/1998 | Pranger |
| D391,594 | S | 3/1998 | Huh |
| 5,768,716 | A | 6/1998 | Porsche |
| 5,802,622 | A | 9/1998 | Baharad et al. |
| 5,809,580 | A | 9/1998 | Arnette |
| 5,815,235 | A | 9/1998 | Runckel |
| 5,818,569 | A | 10/1998 | Berent |
| 5,845,341 | A | 12/1998 | Barthold et al. |
| D405,102 | S | 2/1999 | Moritz et al. |
| 5,867,841 | A | 2/1999 | Chiang |
| D408,431 | S | 4/1999 | Simioni |
| 5,915,542 | A | 6/1999 | Swiet |
| 5,927,281 | A | 7/1999 | Monteleone et al. |
| 5,937,439 | A | 8/1999 | Barthold et al. |
| 5,940,891 | A | 8/1999 | Lane |
| D413,915 | S | 9/1999 | Newcomb et al. |
| 5,966,745 | A | 10/1999 | Schwartz et al. |
| 5,966,746 | A | 10/1999 | Reedy et al. |
| 6,009,564 | A | 1/2000 | Tackles et al. |
| 6,038,707 | A | 3/2000 | Ryden et al. |
| 6,047,410 | A | 4/2000 | Dondero |
| 6,049,917 | A | 4/2000 | Ryden |
| 6,076,196 | A | 6/2000 | Masumoto |
| D428,039 | S | 7/2000 | Thixton |
| 6,092,243 | A | 7/2000 | Wu et al. |
| 6,094,751 | A | 8/2000 | Parks |
| 6,098,204 | A | 8/2000 | Arnette |
| 6,098,205 | A | 8/2000 | Schwartz et al. |
| 6,099,120 | A | 8/2000 | De Lima |
| 6,105,177 | A | 8/2000 | Paulson et al. |
| 6,119,276 | A | 9/2000 | Newcomb et al. |
| 6,138,285 | A | 10/2000 | Robrahn et al. |
| 6,138,286 | A | 10/2000 | Robrahn et al. |
| D439,596 | S | 3/2001 | Bolle |
| D442,206 | S | 5/2001 | Meyerhoffer |
| 6,227,665 | B1 | 5/2001 | Pernicka et al. |
| 6,282,727 | B1 | 9/2001 | Lindahl |
| 6,282,728 | B1 | 9/2001 | Baragar et al. |
| D450,833 | S | 11/2001 | Olivieri |
| 6,321,391 | B1 | 11/2001 | Basso |
| 6,352,387 | B1 | 3/2002 | Briggs et al. |
| D457,545 | S | 5/2002 | Khulusi |
| D457,551 | S | 5/2002 | Khulusi |
| 6,415,452 | B1 | 7/2002 | Watanabe et al. |
| 6,460,196 | B2 | 10/2002 | Tsubooka et al. |
| 6,467,098 | B1 | 10/2002 | Lee |
| D477,010 | S | 7/2003 | Moritz et al. |
| 6,611,965 | B1 | 9/2003 | Lee |
| 6,611,966 | B1 | 9/2003 | Yamamoto et al. |
| 6,615,409 | B2 | 9/2003 | Youmans et al. |
| 6,637,038 | B1 | 10/2003 | Hussey |
| 6,665,885 | B2 | 12/2003 | Masumoto |
| 6,691,324 | B1 | 2/2004 | Nakamura |
| 6,704,944 | B2 | 3/2004 | N Kawaisnshi et al. |
| 6,715,157 | B2 | 4/2004 | Mage |
| 6,718,561 | B2 | 4/2004 | Dondero |
| 6,728,974 | B2 | 5/2004 | Wadsworth |
| 6,732,382 | B2 | 5/2004 | Dondero |
| 6,732,383 | B2 | 5/2004 | Cleary et al. |
| 6,772,448 | B1 | 8/2004 | Hockaday et al. |
| 6,826,785 | B2 | 12/2004 | McNeal |
| D505,444 | S | 5/2005 | Borlet et al. |
| 6,896,366 | B2 | 5/2005 | Rice et al. |
| D509,236 | S | 9/2005 | Sheldon |
| 6,952,841 | B2 | 10/2005 | Schary et al. |
| 6,964,067 | B1 | 11/2005 | Hartman |
| 6,986,169 | B2 | 1/2006 | Nakamura |
| 7,039,959 | B2 | 5/2006 | Dondero |
| 7,052,127 | B2 | 5/2006 | Harrison |
| 7,058,992 | B1 | 6/2006 | Ogonowsky |
| 7,062,797 | B2 | 6/2006 | Khulusi |
| 7,073,208 | B2 | 7/2006 | Penque, Jr. et al. |
| 7,096,514 | B2 | 8/2006 | Khulusi |
| 7,100,215 | B2 | 9/2006 | Shiue |
| 7,137,153 | B2 | 11/2006 | Hussey |
| D537,098 | S | 2/2007 | Sheldon et al. |
| 7,181,779 | B2 | 2/2007 | Hussey |
| 7,192,137 | B2 | 3/2007 | Ishibashi et al. |
| 7,200,875 | B2 | 4/2007 | Dondero |
| D542,327 | S | 5/2007 | Hsu |
| D542,829 | S | 5/2007 | Hsu |
| D542,830 | S | 5/2007 | Hsu |
| 7,260,850 | B2 | 8/2007 | Ambuske et al. |
| D550,749 | S | 9/2007 | Chiang |
| D552,662 | S | 10/2007 | Woxing |
| 7,290,294 | B2 * | 11/2007 | Kita ............... A61F 9/025 2/443 |
| D559,299 | S | 1/2008 | Tabacchi |
| 7,343,631 | B2 | 3/2008 | Liu |
| 7,356,854 | B2 * | 4/2008 | Sheldon ............ A61F 9/027 2/448 |
| 7,370,374 | B2 | 5/2008 | Penque, Jr. et al. |
| 7,404,217 | B2 | 7/2008 | Polinelli et al. |
| 7,407,283 | B2 | 8/2008 | Babineau |
| 7,510,279 | B2 | 3/2009 | Van Atta et al. |
| D591,786 | S * | 5/2009 | Wang ............... D16/312 |
| 7,526,813 | B2 | 5/2009 | Tominaga et al. |
| D598,040 | S | 8/2009 | Sheldon et al. |

(56) References Cited

U.S. PATENT DOCUMENTS

| | | |
|---|---|---|
| D616,915 S | 6/2010 | Silveria et al. |
| D626,166 S | 10/2010 | Yang |
| D626,582 S * | 11/2010 | Cheng ................. D16/326 |
| D640,724 S | 6/2011 | Goodman et al. |
| D649,178 S | 11/2011 | Moritz et al. |
| D649,577 S | 11/2011 | Goodman et al. |
| 8,166,578 B2 * | 5/2012 | Tan ................. A61F 9/025 2/427 |
| D669,113 S | 10/2012 | Sandor et al. |
| D675,244 S | 1/2013 | Orzeck et al. |
| D685,839 S * | 7/2013 | Pearson ............. D16/312 |
| D687,479 S | 8/2013 | Moritz et al. |
| D687,881 S * | 8/2013 | Ginther ............. D16/312 |
| D688,296 S | 8/2013 | Pearson et al. |
| D695,335 S * | 12/2013 | Goodman ........... D16/312 |
| 2002/0148034 A1 | 10/2002 | Lee |
| 2002/0157175 A1 | 10/2002 | Dondero |
| 2003/0110552 A1 | 6/2003 | Youmans et al. |
| 2005/0128426 A1 * | 6/2005 | Shiue ............ A63B 33/002 351/43 |
| 2006/0048289 A1 | 3/2006 | Shiue |
| 2006/0191062 A1 | 8/2006 | Matera |
| 2006/0272078 A1 | 12/2006 | Polinelli et al. |
| 2007/0033718 A1 * | 2/2007 | Lin ................. G02C 11/08 2/448 |
| 2008/0109949 A1 | 5/2008 | Kinsella |
| 2009/0019620 A1 * | 1/2009 | Reed ............. A61F 9/025 2/438 |
| 2009/0038059 A1 | 2/2009 | McNeal et al. |
| 2009/0122258 A1 | 5/2009 | Fielding, Jr. |
| 2012/0038879 A1 * | 2/2012 | Reyes ............ A61F 9/025 351/107 |
| 2014/0033408 A1 | 2/2014 | Currens et al. |
| 2014/0157496 A1 * | 6/2014 | Ginther ........... A61F 9/025 2/439 |

FOREIGN PATENT DOCUMENTS

| | | |
|---|---|---|
| DE | 2943472 | 5/1981 |
| EP | 0504518 | 8/1991 |
| EP | 1095577 | 7/2000 |

* cited by examiner

GOGGLE LENS CHANGING SYSTEM

CROSS-REFERENCE TO RELATED APPLICATIONS

This application claims the benefit of U.S. Provisional Application No. 62/864,842, filed Oct. 16, 2014, the contents of which are expressly incorporated herein by reference.

STATEMENT RE: FEDERALLY SPONSORED RESEARCH/DEVELOPMENT

Not Applicable

BACKGROUND

The various embodiments and aspects described herein relate to a lens changing system to allow a user to switch lenses out of a google.

Currently, goggles typically have a fixed lens system meaning that the lens cannot be removed from the frame without destroying either the lens or the frame. In this regard, if the user encounters different lighting conditions during use of the goggle, the user may continue to wear a goggle having a lens that is unfit for the particular lighting condition, or as an alternative, the user may carry two goggles in order to switch out the goggles based on the particular lighting condition. By way of example and not limitation, while engaging in snow sports, a portion of the day may be bright without cloud cover while a different portion of the day may be overcast. Unfortunately, this presents two different lighting conditions for the snow sport participant. In bright lighting conditions, the optimal lens would be a lens with a darker tint. In overcast conditions, the optimal lens would be a lens with a lighter tint. If the user uses a goggle having a lens with a light tint, then this would be suboptimal for the bright lighting conditions. Conversely, if the user uses a goggle having a lens with a darker tint then this would be suboptimal for the overcast conditions.

Goggles having interchangeable lenses have been introduced into the marketplace so that the user can install the proper lens for the current lighting condition. However, these interchangeable lens systems have one or more deficiencies that may make changing the lens suboptimal.

Accordingly, there is a need in the art for a goggle having an improved system for changing the goggle lenses.

BRIEF SUMMARY

A goggle for use in an active sport is disclosed herein which has a lens changing system for allowing the user to switch out the lens as needed to accommodate a particular lighting condition or replace a defective lens. The lens changing system includes a sliding lever that is traversable between a closed position and an opened position. In the closed position, the lens is disposed between the sliding lever and the frame in order to retain the lens to the frame during use of the goggle in the active sport. In the opened position, the sliding lever is traversed away from the lens to allow the lens to be removed from the frame in order to change out the lens to a more appropriate lens depending on the anticipated use of the goggle or to replace the current lens which may be defective. Additionally, the lens changing system includes a nub that may be formed on the frame and a receiving hole formed in the lens that receives the nub to further secure the lens to the frame when the sliding lever is in the closed position.

More particularly, a sports goggle for providing protection to eyes of a participant of an active sport is disclosed. The goggle may comprise a frame, a lens and an attachment mechanism. The frame may have a proximal side and a distal side. The proximal side may be configured to mate with a face of the participant. The frame may have an aperture through which a scene is visible by the participant. The frame may define an outer peripheral portion. The lens may have an outer peripheral portion shaped to match the outer peripheral portion of the frame.

The attachment mechanism may be formed on the frame and lens. The attachment mechanism may comprise a nub, a receiving hole and a sliding lever. The nub may be formed on one of the outer peripheral portion of the frame and the lens. The receiving hole may receive the nub and be formed on the other one of the outer peripheral portion of the frame and the lens. The sliding lever may be traversable away from the lens to an open position or over the lens to a closed position. If traversed to the open position, the lens may be removed from the frame. If traversed to the closed position, the lens is retained on the frame during participation of the sport by the participant.

The frame may have an elongate slot formed in the outer peripheral portion. The slot may define a narrow section with opposed enlarged sections which are wider than the narrow section. The sliding lever may have a detent having a thickness greater than a width of the narrow section. The detent may be traversable between the opposed enlarged sections with hand pressure on the sliding lever.

The sliding lever is in the closed position when the detent of the sliding lever is in one of the opposed enlarged sections such as the medial enlarged section. The sliding lever is in the open position when the detent of the sliding lever is in the other one of the opposed enlarged sections such as the lateral enlarged section.

The nub may be formed on the outer peripheral portion of the frame. The receiving hole that receives the nub may be formed on a lateral end portion of the lens. If there are two or more nubs and receiving holes, then the nubs may be formed on opposed left and right sides of the outer peripheral portion of the frame and the receiving holes may be formed on lateral left and right end portions of the lens.

The lens may be fabricated from an acrylic material. The lens may be injection molded.

In another aspect, a method for switching a first lens mounted to a frame of a goggle with a second lens is disclosed. The method may comprise the steps of sliding a lever away from an edge of the lens so that the first lens is removable from the frame of the goggle; disengaging a nub and a receiving hole formed on the first lens and frame to enable removal of the first lens from the frame; engaging the nub and the receiving hole formed on the second lens and frame; and sliding the lever over the edge of the lens so that the second lens is retained on the frame during use of the goggle in an active sport.

The sliding the lever steps may include the step of traversing a detent of the sliding lever to opposed sides of a narrow section of an elongate slot formed in an outer peripheral portion of the frame.

The sliding the lever over the edge of the lens step may include the step of sliding the lever over the nub.

BRIEF DESCRIPTION OF THE DRAWINGS

These and other features and advantages of the various embodiments disclosed herein will be better understood with respect to the following description and drawings, in which like numbers refer to like parts throughout, and in which.

DETAILED DESCRIPTION

Figure 1:
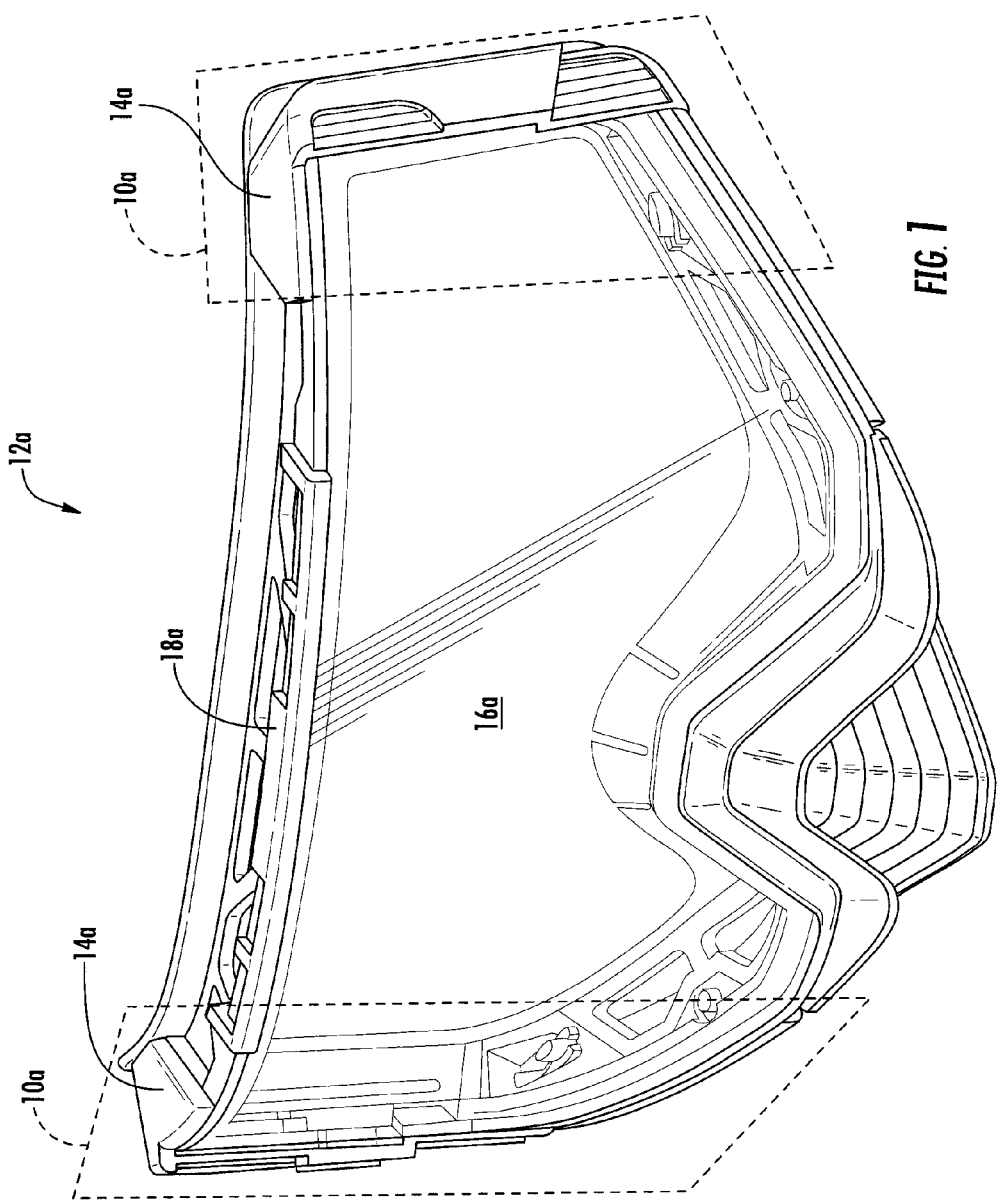
FIG. 1 is a perspective view of a motocross goggle having a lens changing system.
Figure 2:
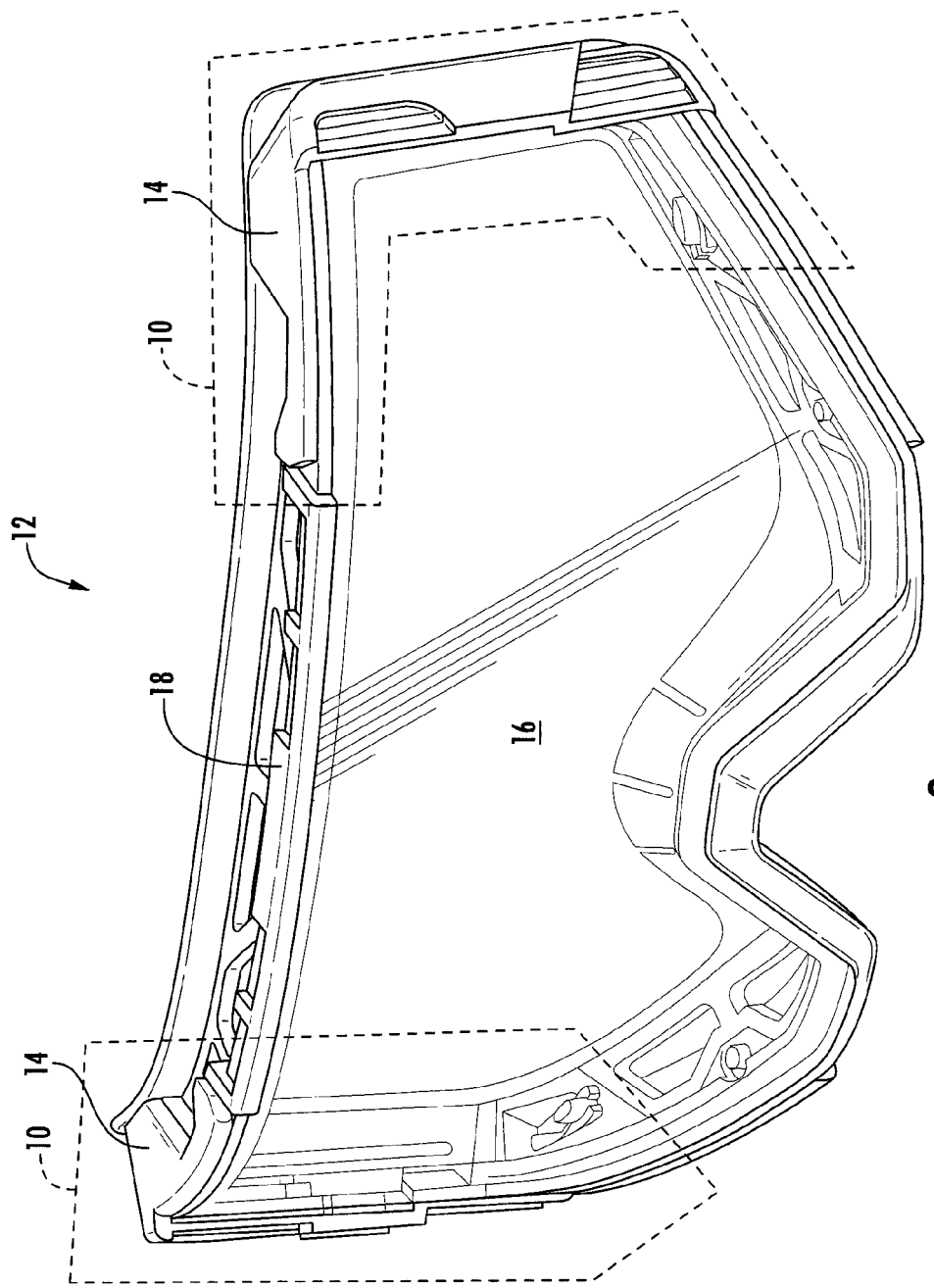
FIG. 2 is a perspective view of a snow goggle having the lens changing system.

Referring now to the drawings, a lens changing system 10, 10a for a goggle 12, 12a is shown. The lens changing system 10, 10a includes a sliding lever 14, 14a that is traversable between a closed position (see FIG. 3) and an open position (see FIG. 4) to either retain a lens 16, 16a on a frame 18, 18a of the goggle 12, 12a or to allow removal of the lens 16, 16a from the frame 18, 18a to change out the current lens 16, 16a to a different lens 16, 16a. The lens changing system 10, 10a also includes a nub 20 (see FIG. 7) and a receiving hole 22 (see FIG. 7) formed on the frame 18 and lens, respectively, to position and/or retain the lens 16 on the frame 18. The lens changing system 10 allows the user to mount a specific lens 16 to the frame 18 for a particular purpose. By way of example and not limitation, a clear transparent lens 16 may be mounted to the frame 18 for lowlight conditions, whereas, a tinted transparent lens 16 may be mounted to the frame 18 for bright light conditions. Also, the lens changing system 10 allows the user to replace the current lens if defective with a new lens.

Figure 6:
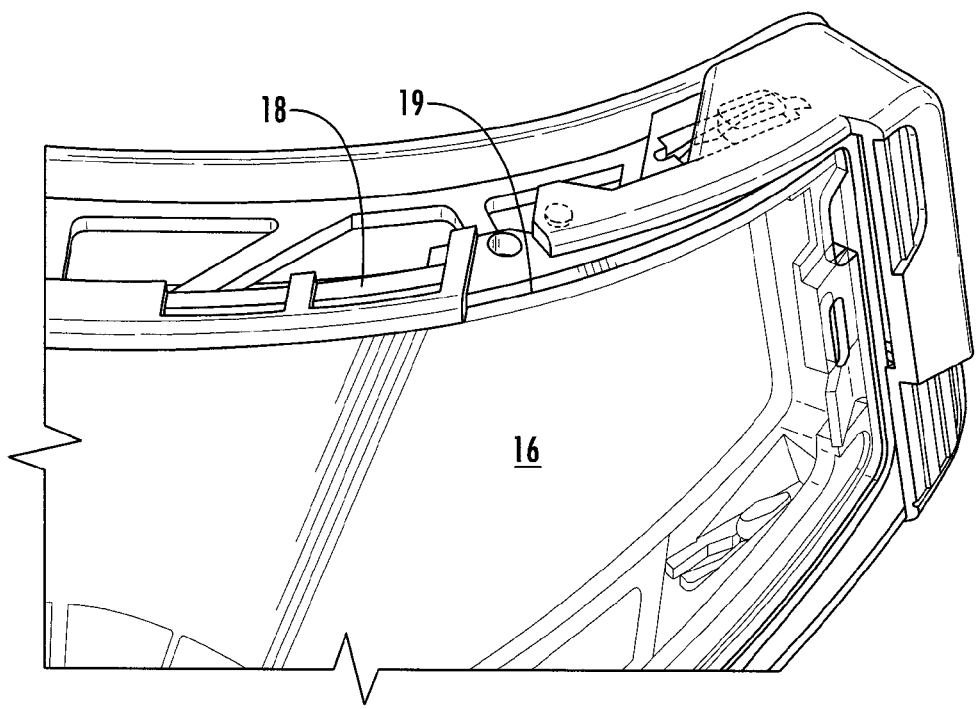
FIG. 6 is an enlarged perspective view of the right side of the snow goggle shown in FIG. 2 with the sliding lever disposed in the opened position.
Figure 7:
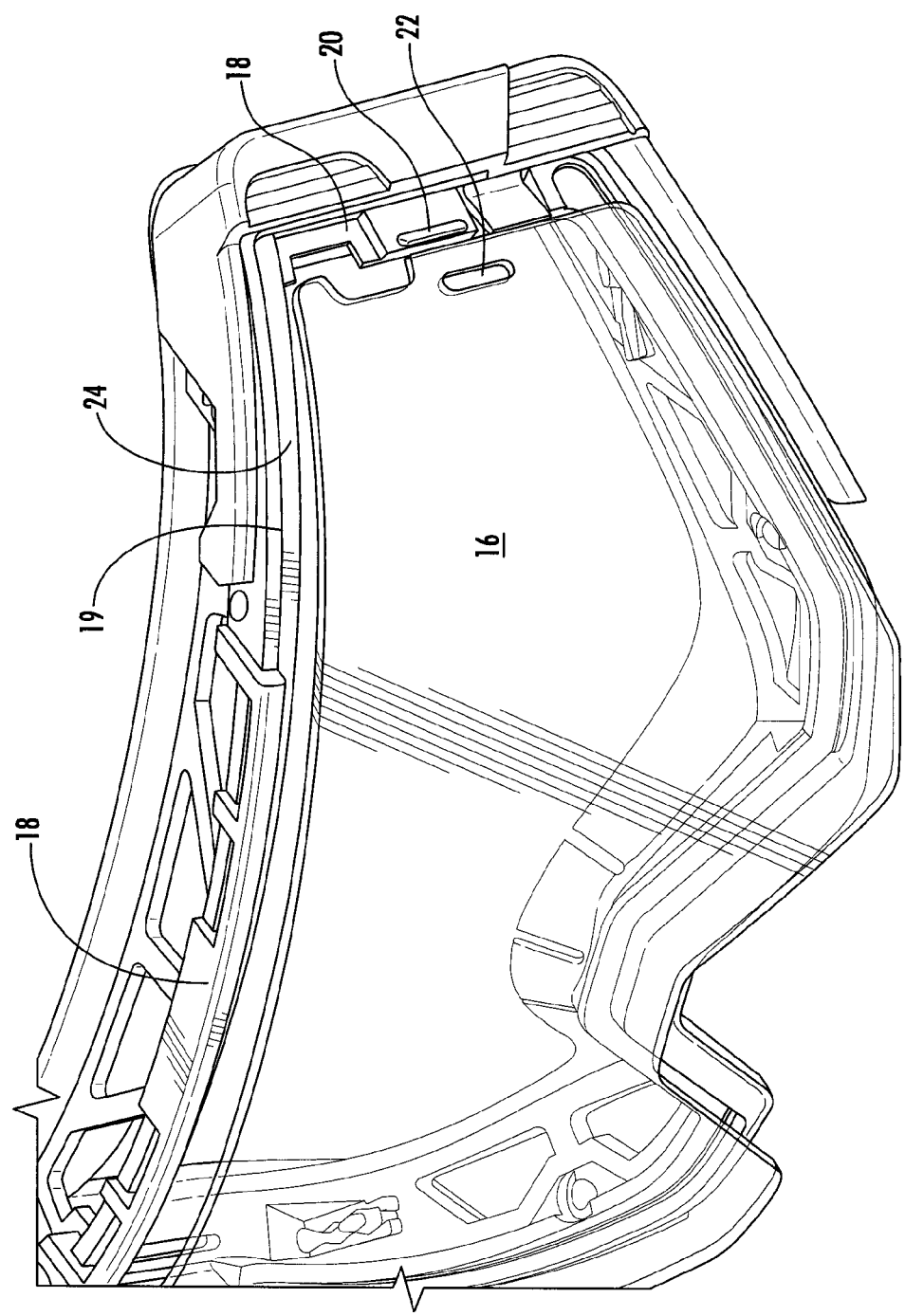
FIG. 7 is an enlarged perspective view of the right side of the snow goggle shown in FIG. 2 with the sliding lever disposed in the opened position and a lens removed from a frame of the snow goggle.

More particularly, referring to FIG. 1, the lens 16 may be sized and configured to fit the frame 18 of the goggle 12. The frame 18, as shown in FIG. 7 may have a recess 19. The lens 16 may fit within the recess 19 as shown in FIG. 6. The lens 16 may be curved to provide a wide viewing angle to the wearer during use of the goggle 12. The curvature of the lens 18 may be matched to a curvature of an interface surface 24 (see FIG. 7) of the frame 18 so that air does not flow between the lens 16 and the frame 18 during use. To further mitigate airflow between the lens 16 and the frame 8, a gasket (not shown) may be attached to the interface surface 24 of the frame 18 or an interior side of the lens 16 at an outer periphery of the lens 16. The gasket contacts the interface surface 24 of the frame 18 and the lens 16 when the lens 16 is mounted to the frame 18.

Figure 10:
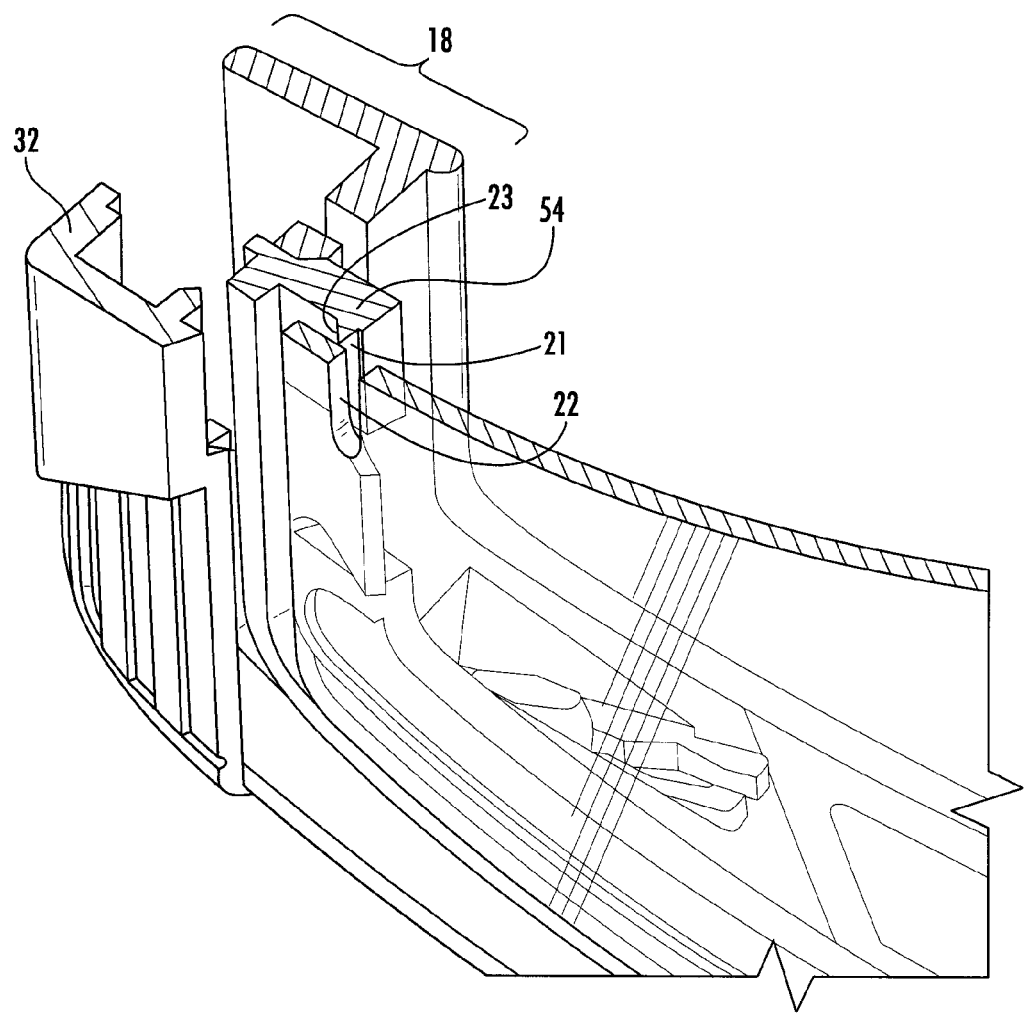
FIG. 10 illustrates the view shown in FIG. 9 with the lens removed from the frame.

The lens 16 may be fabricated from an acrylic material, or similar material known in the art, so that the curvature of the lens 16 is retained even when the lens 16 is not mounted to the frame 18. The acrylic material may be injection molded into the curved shape of the lens 16. By fabricating the lens 16 to be rigid and curved, the lens 16 may be more positively engaged to the frame 18. In particular, the lens 16 may also have a receiving hole 22 (see FIG. 7) for receiving a nub 20 formed on the frame 18. The receiving hole 22 is disposed over the nub 20, as shown in FIG. 6. The nub 20 may have an outward orientation and be disposed on the frame 18, as shown in FIG. 7. The nub 20 may have a medial flat surface 21 and a lateral angled surface 23, as shown in FIG. 10. The medial flat surface 21 may be generally perpendicular to a curvature of the lens 16 and to the corresponding interface surface 24 of the frame 18. The angled lateral surface 23 is skewed toward the center of the goggle 10 so that the lens 16 does not need to be deformed in order to insert the nub 20 formed on the frame 18 into the receiving hole 22 of the lens 16. However, it is also contemplated that the lateral surface 23 may be perpendicular to the curvature of the lens 16 and the interface surface 24 of the frame 18 so that the user would have to deform the lens 16 and/or the frame 18 so that the nub 20 formed on the frame may be inserted into the receiving hole 22 of the lens 16.

The lens 16 may be formed with two receiving holes 22. One receiving hole 22 may be formed in each of the lateral left and right sides of the lens 16, as shown in FIGS. 7 and 10. Corresponding nubs 20 may be formed on opposing lateral left and right sides of the frame 18 and are configured to be insertable into the receiving holes 22 formed in the lens 16. Although the lens 16 is described as having two receiving holes 22 and the frame 18 having two corresponding nubs 20, it is also contemplated that the lens 16 may have one left or right receiving hole 22 and the frame 18 may have a corresponding single left or right nub 20 to secure the lens 16 to the frame 18. The other side of the lens 16 (i.e., right or left side) may be secured to the frame 18 by forming a groove within that side of the frame 18. The opposite lateral edge of the lens 16 without the receiving hole 22 may be initially wedged into the groove of the frame 18. The lens 16 is traversed and rotated in order to insert the nub 20 into the receiving hole 22 of the lens 16. Moreover, the lens changing system 10 is described with the receiving hole 22 formed in the lens 16 and the nub 20 formed in the frame 18. However, it is also contemplated that the lens changing system 10 may be configured in the opposite configuration, namely, the nub 20 may be formed on the lens 16 and protrude inward and be insertable into a cavity or hole 22 formed in the frame 18. The various aspects and features described in relation to the embodiment shown and described herein may be applied to these other contemplated configurations.

Figure 3:
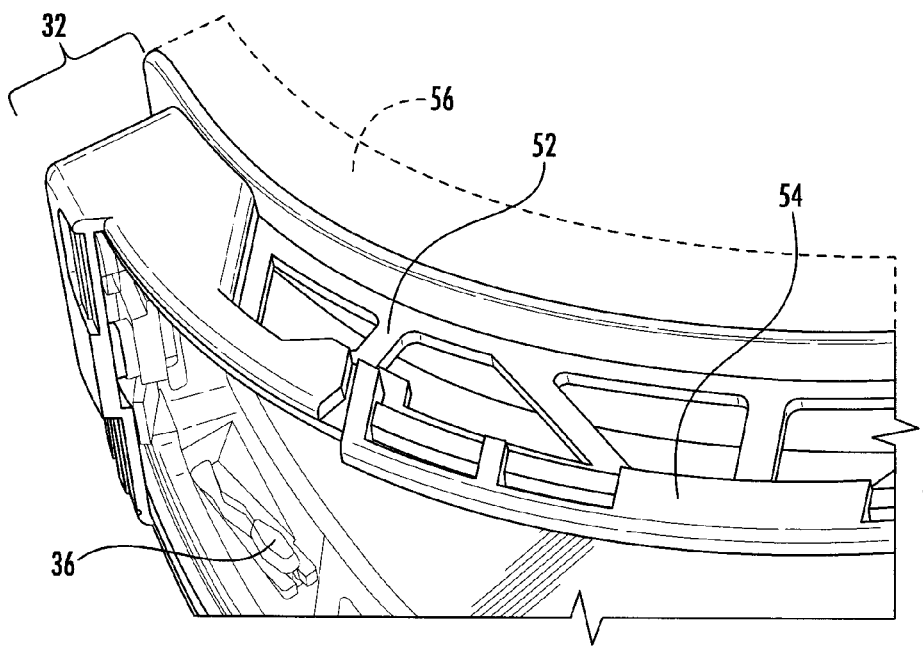
FIG. 3 is an enlarged perspective view of a left side of the snow goggle shown in FIG. 2 with a sliding lever disposed in a closed position.

The frame 18 may be formed as a unitary component or fabricated from a plurality of components that are attached to each other to provide the support necessary to space the lens 16 a fixed distance away from the wearer's eyes and to prevent particulate (e.g., snow, dirt, debris) from bypassing the lens 16 and disturbing the wearer's eyes. Referring to FIG. 3, the frame 18 may be fabricated from three different components, namely, a cushion 56 which interfaces or contacts the user's face, an intermediate frame member 52 and a distal frame member 54. The intermediate frame member 52 may be semi-rigid to provide form to the goggle 10. The distal frame member 54 may be sufficiently rigid to allow the lens changing system 10 to function. The nub 20 may be formed on the lateral sides of the frame 18. Once the lens 16 is disposed within the recess 24 of the frame 18 and the nubs 20 in the corresponding receiving holes 22, the lens 16 may be secured to the frame 18 with sliding levers 32, as shown in FIGS. 3 and 4.

Figure 4:
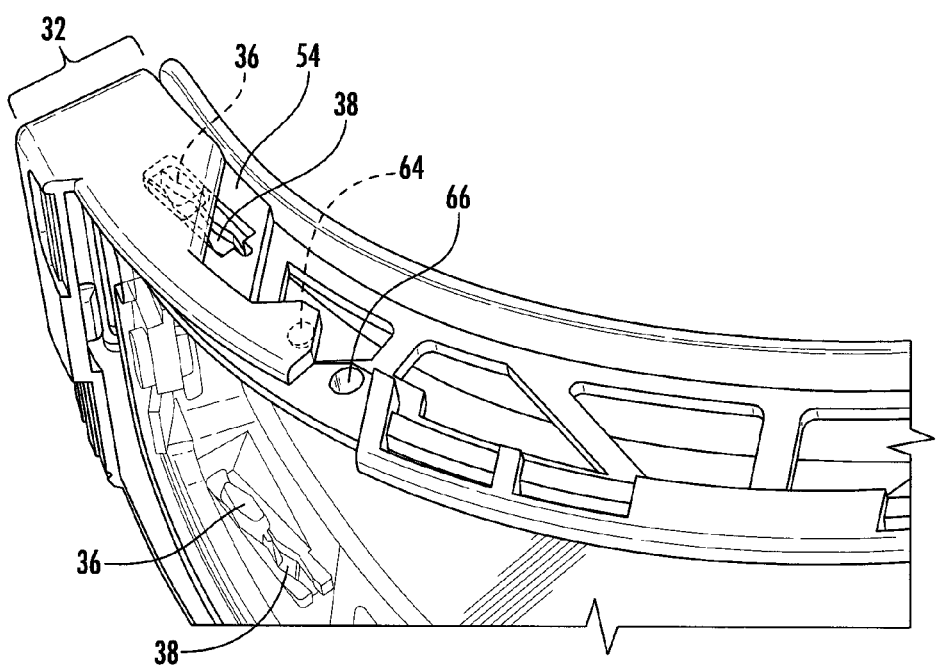
FIG. 4 is an enlarged perspective view of a left side of the snow goggle shown in FIG. 2 with a sliding lever disposed in an opened position.
Figure 8:
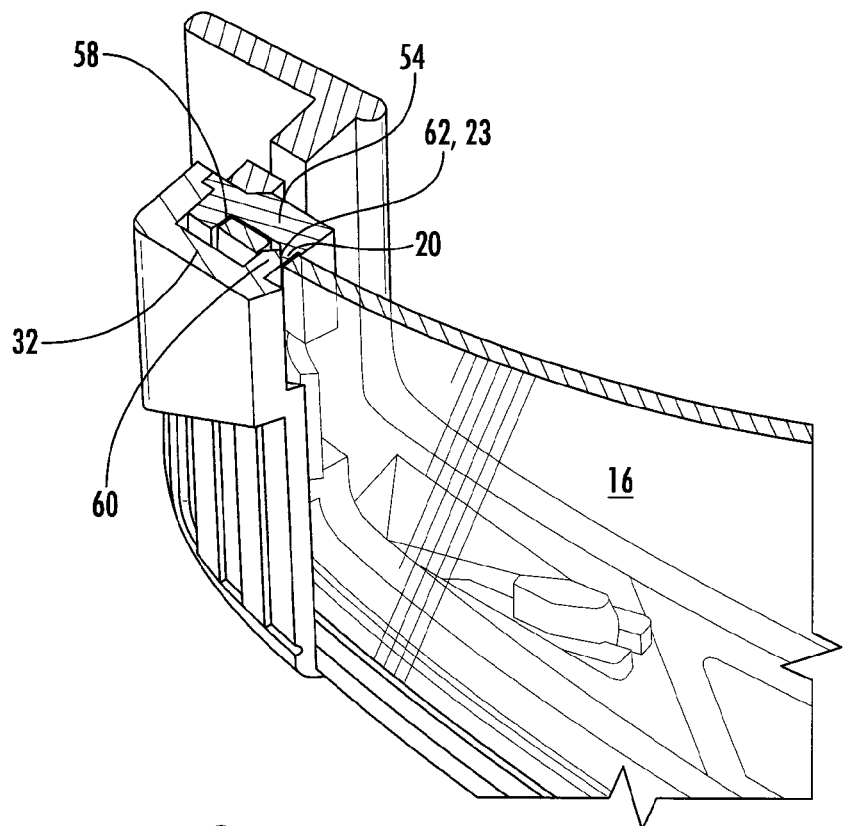
FIG. 8 is a cross-sectional view of the left side of the snow goggle illustrating the interaction between the sliding lever, a nub formed on the frame and the receiving hole formed in the lens with the sliding lever in the closed position.
Figure 9:
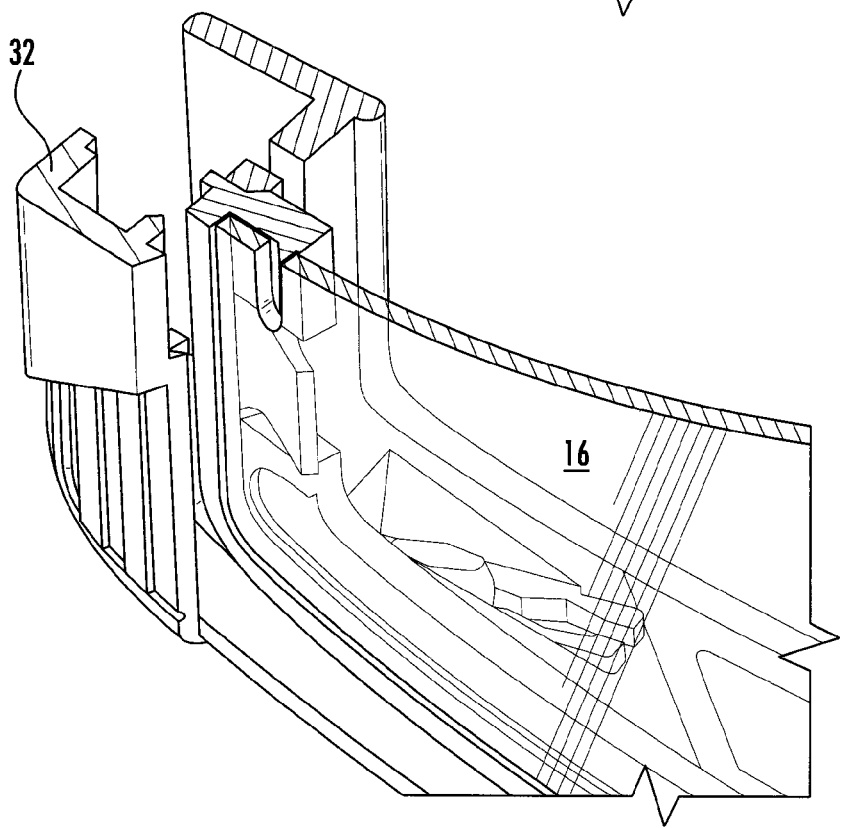
FIG. 9 illustrates the view shown in FIG. 8 with the sliding lever in the opened position.

The sliding levers 32 may be traversed between a closed position (see FIG. 3) and an open position (see FIG. 4). In the closed position, as shown in FIG. 8, the sliding lever 32 sandwiches the edge 58 of the lens 16 between the sliding lever 32 and the frame 18, and more particularly between the sliding lever 32 and the distal frame member 54. This prevents the lens 16 from inadvertently dislodging from the frame 18 during use. Moreover, in the closed position, the sliding lever 32 may be disposed over the nub 20 and in contact with a top surface of the nub 20 to securely capture the nub 20 within the receiving hole 22. This further secures the lens 16 to the frame 18. More particularly, referring to FIG. 8, the sliding lever 32 may have an inwardly extending protrusion 60. This protrusion 60 mates with the nub 20 in that the protrusion 60 may have a corresponding angled surface 62 that mates up with the angled surface 23 of the nub 20. Moreover, the protrusion 60 fills up the space within the receiving hole 22 of the lens 16 to prevent the lens 16 from rattling or wiggling once the sliding lever 32 is traversed to the closed position.

Figure 4A:
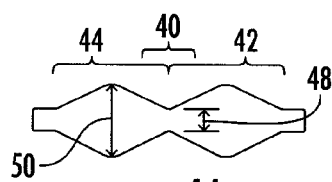
FIG. 4A is an enlarged top view of a slot of the lens changing system in which a detent slides back and forth.
Figure 5:
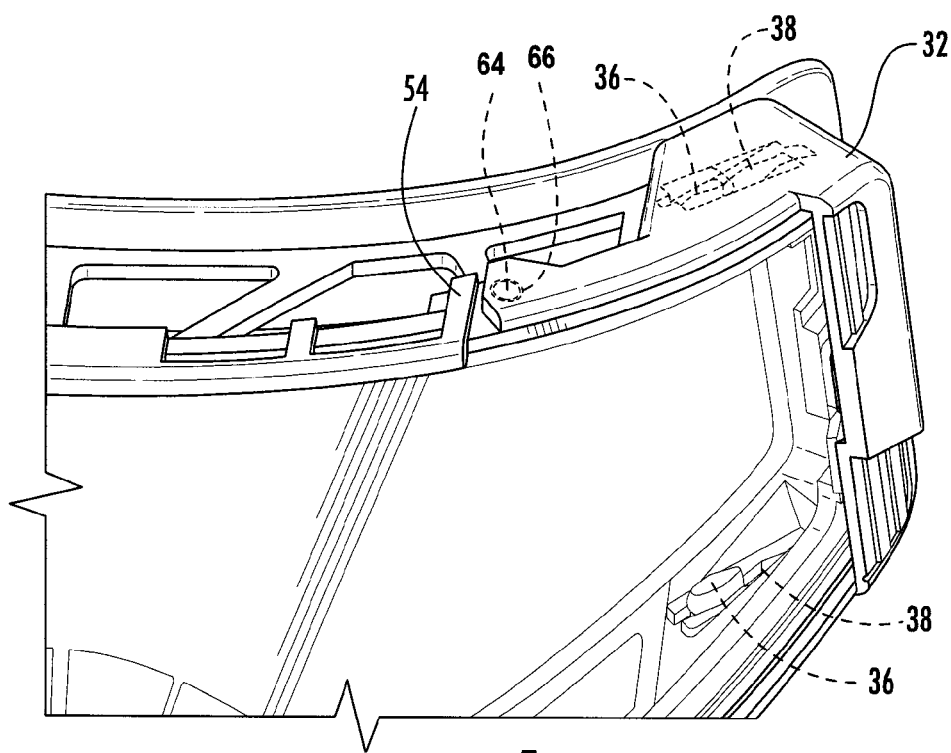
FIG. 5 is an enlarged perspective view of the right side of the snow goggle shown in FIG. 2 with the sliding lever disposed in a closed position.

The sliding levers 32 may each have one or more detents 36. As shown in FIGS. 4 and 5, each of the sliding levers 32 has two detents 36. One detent 36 is located at the top of the sliding lever 32. Another detent 36 is located at the bottom of the sliding lever 32. Each detent 36 is received into an elongate slot 38 formed in the frame 18, and more particularly, formed in the distal frame member 54. The elongate slot 38 may have a narrow section 40 and opposed enlarged sections 42, 44, as more clearly shown in FIG. 4A. The detent 36 may define a thickness 46 which is greater than a width 48 of the narrow section 40 of the elongate slot 38. In this manner, when the detent 36 is disposed in the enlarged section 42, the interference between the detent 36 and the narrow section 40 prevents the detent 36 from being traversed to the other enlarged section 44. The converse may also be true. When the detent 36 is in the enlarged section 40, the interference between the detent 36 and the narrow section 40 prevents the detent 36 from being traversed to the other enlarged section 42 without user intervention. Hence the detent 36 and the narrow section 40 prevents the detent 36 from being inadvertently traversed to the other enlarged section 42, 44. The interference between the detent 36 and the narrow section 40 mitigates inadvertent traversal of the sliding lever 32 between the closed and open position.

Figure 4B:
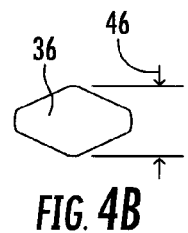
FIG. 4B is an enlarged top view of the detent that slides within the slot shown in FIG. 4A.

The enlarged sections 42, 44 may also define a width 50 which is equal to or slightly greater than the thickness 46 of the detent 36. Preferably, the width 50 of the enlarged sections 42, 44 is equal to thickness 46 of the detent 36 to prevent rattling of the sliding lever 32. More preferably, as shown in FIGS. 4A and 4B, the detent 36 may have an outer peripheral shape (e.g., diamond shape) which matches the inner peripheral shape (e.g., diamond shape) of the enlarged sections 42, 44. The diamond shape of the detent 36 also assists in traversing the detent 36 between the opposed enlarged sections 42, 44. In order to move the detent 36 between the enlarged sections 42, 44, the narrow section 48 and/or the detent 36 may be fabricated from a deformable material so that the narrow section 40 can be bent or the detent 36 compressed to allow the detent 36 to pass by the narrow section 40.

The goggle 12 may be provided with a plurality of different lenses 16. A first lens 16 may be a clear or lightly tinted transparent lens for low light conditions (e.g., nighttime or cloudy daytime use). A second lens 16 may have a heavier tint compared to the first lens 16 and may be primarily used for bright light conditions. In order to mount the first lens 16 to the frame 18 of the goggle 12, the user traverses the sliding levers 32 located on the left and right sides of the frame 18 to the open position if they are not already in the open position. The user moves the sliding lever 32 to the open position by gripping or frictionally engaging the sliding lever 32 and pushing it outwards, as shown in FIGS. 3 and 4. The sliding levers 32 on both sides of the goggle 10 are traversed to the open position. By pushing the sliding levers 32 outward, the detent 36 is traversed from the medial enlarged section 42 to the lateral enlarged section 44 of the elongate slot 38. The sliding levers 32 move away from the nubs 20 formed on the lateral sides of the frame 18 and also move away from an edge of the lens 16 that may currently be mounted to the frame 18, as shown in FIGS. 5 and 6 and FIGS. 8 and 9. If the lens 16 is currently mounted to the frame 18, then the user disengages the nubs 20 from the holes 22, as shown in FIGS. 7 and 10.

The user pops the lens 16 off of the frame 18, as shown in FIGS. 7 and 10. The user may grab the first or second lenses 16 depending on the particular environmental conditions that the user finds themselves in, in order to mount a lens 16 that is suitable for the intended environmental condition. By way of example and not limitation, the user may grip the first lens 16 and position the first lens 16 over the frame 18 and align the receiving holes 22 formed in the lens 16 over the nubs 20 formed in frame 18. One of the nubs 20 is inserted into the corresponding hole 22, the other nub 20 is inserted into the other hole 22. With the nubs 20 in the receiving holes 22, the user may now traverse the sliding levers 14 to the closed position.

To traverse the sliding levers 14 to the closed position, the user pushes on the outer sides of the sliding levers 14 inward toward the central part of the frame 18. In doing so, the detent 36 is traversed from the lateral enlarged section 44 to the medial enlarged section 42. Also, the detent 36 deforms the narrow section 40 to allow the detent 36 to pass therethrough. Moreover, once the detent 36 is disposed within the enlarged section 42, the sliding levers 14 do not rattle since the size and shape of the detent 36 is similar in size and shape to the elongate slot 38 at the lateral enlarged sections 44.

Referring now to FIG. 4, and according to one embodiment, the sliding levers 32 may have a protrusion 64 that can be disposed within a recess 66 formed in the distal frame member 54 of the frame 18. In the opened position, the protrusion 64 is not disposed within the recess 66. However, when the sliding levers 32 are traversed to the closed position, the protrusion 64 is disposed within the recess 66 to further retain the sliding levers 32 in the closed position. The protrusion 64 and corresponding recess 66 is optional as these features are not shown in the goggle shown in FIG. 1. Although the embodiment depicted in FIG. 4 includes a protrusion 64 formed on the sliding lever 32, it is expressly contemplated that the protrusion 64 is an optional feature, which may not be included in other embodiments of the goggle.

The lens 16 may be a single pane lens or a dual pane lens as is common in the art of goggles. The features and aspects described herein may also be applied to eyeglasses. Each of the lenses of the eye glasses may have one or two sliding levers 14 that lock the lenses into each of the lens receiving portions of the frame. Preferably, there may be one sliding lever 14 on the lateral sides of the lens receiving portions of the frame. The medial side of the lenses are received in a groove or cavity on a medial area of the lens receiving portion of the frame that locks the lenses 16 into place.

Although not shown, a conventional post system for use with conventional protective multi layered removable lens may be incorporated into the frame of the goggle 10, 10a.

The above description is given by way of example, and not limitation. Given the above disclosure, one skilled in the art could devise variations that are within the scope and spirit of the invention disclosed herein, including various ways of forming the lenses 16. Further, the various features of the embodiments disclosed herein can be used alone, or in varying combinations with each other and are not intended to be limited to the specific combination described herein. Thus, the scope of the claims is not to be limited by the illustrated embodiments.

What is claimed is:

1. A sports goggle for providing protection to eyes of a participant of an active sport, the goggle comprising:
   a frame having a proximal side and a distal side, the proximal side configured to mate with a face of the participant, the frame having an aperture through which a scene, is visible by the participant, the frame defining an outer peripheral portion;
   a lens having an outer peripheral portion shaped to match the outer peripheral portion of the frame;
   an attachment mechanism formed on the frame and lens, the attachment mechanism comprising:
      a nub formed on one of the outer peripheral portion of the frame and the lens;
      a receiving hole for the nub formed on the other one of the outer peripheral portion of the frame and the lens;
      a sliding lever that is traversable away from the lens to an open position so that the lens is removable from the frame and over the lens to an closed position so that the lens is retained on the frame during participation of the sport by the participant;
   wherein the frame has an elongate slot formed in the outer peripheral portion, the slot defining a narrow section disposed between opposed enlarged sections, and the sliding lever has a detent having a thickness greater than a width of the narrow section and traversable between the opposed enlarged sections with hand pressure on the sliding lever.

2. The goggle of claim 1 wherein the sliding lever is in the closed position when the detent of the sliding lever is in one of the opposed enlarged sections, and the sliding lever is in the open position when the detent of the sliding lever is in the other one of the opposed enlarged sections.

3. A method for switching a first lens mounted to a frame of a goggle with a second lens, the method comprising the steps of:
   sliding a lever away from an edge of the lens so that the first lens is removable from the frame of the goggle;
   disengaging a nub and a receiving hole formed on the first lens and frame to enable removal of the first lens from the frame;
   engaging the nub and the receiving hole formed on the second lens and frame; and
   sliding the lever over the edge of the lens so that the second lens is retained on the frame during use of the goggle in an active sport;
   wherein the sliding the lever steps includes the step of traversing a detent of the sliding lever to opposed sides of a narrow section of an elongate slot formed in an outer peripheral portion of the frame.

4. A selectively configurable goggle comprising:
   a frame disposed about a frame opening and defining a frame outer peripheral portion, the frame including a first engagement element;
   a lens having a second engagement element complimentary to the first engagement element, and a lens outer peripheral portion complimentary to the frame outer peripheral portion, the lens being selectively positionable over the frame opening, the first engagement element and second engagement element being engaged with each other when the lens is positioned over the frame opening; and
   a sliding lever that is traversable away from the lens to an open position so that the lens is removable from the frame and over the lens to an closed position so that the lens is retained on the frame;
   wherein the first engagement element includes a nub formed on the frame outer peripheral portion; and
   further comprising a third engagement element coupled to the sliding lever and advanceable through the receiving hole.

5. The selectively configurable goggle of claim 4, wherein the third engagement element includes a protrusion extending from the sliding lever and adapted to engage with the nub when the sliding lever is in the closed position.

6. The selectively configurable goggle of claim 4 wherein the frame has an elongate slot formed in the frame outer peripheral portion, the slot defining a narrow section with disposed between opposed enlarged sections, and the sliding lever has a detent having a thickness greater than a width of the narrow section and traversable between the opposed enlarged sections with hand pressure on the sliding lever.

7. The selectively configurable goggle of claim 6 wherein the sliding lever is in the closed position when the detent of the sliding lever is in one of the opposed enlarged sections, and the sliding lever is in the open position when the detent of the sliding lever is in the other one of the opposed enlarged sections.

* * * * *